US00PP09482P

United States Patent [19]

Olesen et al.

[11] Patent Number: Plant 9,482

[45] Date of Patent: Mar. 26, 1996

[54] MINIATURE ROSE PLANT NAMED 'POULPRIMA'

[75] Inventors: Mogens N. Olesen; Pernille Olesen, both of Fredensborg, Denmark

[73] Assignee: Bear Creek Gardens, Inc., Medford, Oreg.

[21] Appl. No.: 409,754

[22] Filed: Mar. 24, 1995

[51] Int. Cl.[6] ..... A01H 5/00

[52] U.S. Cl. ..... Plt./10

[58] Field of Search ..... Plt./7.1, 10, 22, Plt./26–29

*Primary Examiner*—Howard J. Locker

*Attorney, Agent, or Firm*—Klarquist Sparkman Campbell Leigh & Whinston

[57] ABSTRACT

A new rose variety of the miniature class having a compact, vigorous growth habit; excellent post-harvest shelf life; ease of propagation by softwood cuttings; larger foliage and flowers than POULvic; and flowers borne in clusters.

1 Drawing Sheet

The present invention relates to a new and distinct variety of rose plant of the miniature class which was originated by me by crossing the variety POULvic, U.S. Plant Pat. No. 8,012, with an unnamed seedling.

The primary objective of this breeding was to produce a new rose variety having the compact habit, upright vigorous growth, clustering flower habit, long shelf life as a pot rose, and prolific bloom of the female parent combined with the larger foliage and flowers of the male parent. The objective was substantially achieved, along with other desirable improvements, as evidenced by the following unique combination of characteristics that are outstanding in the new variety and that distinguish it from its parents, as well as from all other varieties of which I am aware and make it an ideal pot rose:

1. Compact, vigorous growth habit.
2. Excellent shelf life.
3. Ease of propagation by soft wood cuttings.
4. Larger foliage and flowers than POULvic
5. Flowers borne in clusters.

Asexual reproduction of this new variety by softwood cutting, as performed at Wasco and Somis, Calif. and Fredensborg, Denmark, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—POULvic, U.S. Plant Pat. No. 8,012.

*Pollen parent.*—Unnamed seedling.

Classification:

*Botanical.*—Rosa hybrida.

*Commercial.*—Miniature.

FLOWER

Observations made from specimens grown in a greenhouse environment at Somis, Calif. and at Fredensborg, Denmark.

Blooming habit: Continuous.

Bud:

*Size.*—One inch long when the petals start to unfurl.

*Form.*—The bud form is pointed ovoid.

*Color.*—When sepals first divide, bud color is Red-Purple Group 61C. When half blown, the upper sides of the petals are Red-Purple Group 61C; and the lower sides of the petals are Red-Purple Group 61C.

*Sepals.*—Color: Green Group 138B. Surface texture: Covered in fine hairs. There are three normally appendaged sepals. There are two unappendaged sepals with hairy edges.

*Receptacle.*—Color: Green Group 139C. Shape: Apple. Size: Small (3/16"×3/16"). Surface: Smooth.

*Peduncle.*—Length: Short (3/4" to 1"). Surface: Smooth. Color: Medium green. Strength: Stiff and erect.

Bloom:

*Size.*—Small. Average open size is 1¾ to 2 inches.

*Borne.*—Singly and several together, in clusters of 3–5 flowers.

*Stems.*—Short and strong. Average length is about 6" to 8".

*Form.*—When first open: High centered. Permanence: Flattens, and outer petals curl back.

*Petalage.*—Number of petals under normal conditions: 30–35.

*Color.*—The upper side of the petals is Red-Purple Group 61C. The reverse side of the petals is Red-Purple Group 61C. The base of each petal has a small half-moon at its point of attachment that is Yellow Group 4A on the inner surface and Yellow Group 4C on the outer surface. The major color on the upper side is Red-Purple Group 61C.

*Variegations.*—There is an occasional white streak on the guard petals.

*Discolorations.*—The general tonality at the end of the first day: No change. At the end of the third day: No change. By day 6 or 7, there is a fading to Red-Purple Group 61D.

*Fragrance.*—Slight.

Petals:

Texture.—Thick.

*Shape.*—Deltoid.

*Form.*—Flat, with tips slightly recurved.

*Arrangement.*—Imbricated, with few petaloids in the center.

*Persistence.*—Drop off cleanly.

*Lastingness.*—On the plant: Very long (12–14 days). As a cut flower: Not tested.

Reproductive parts:

*Anthers.*—Size: Medium. Quantity: Many. Color: Yellow. Arrangement: Regular round styles.

*Filaments.*—Color: White.

*Pollen.*—Color: Lemon yellow.

*Styles.*—Color: Greenish-white.

*Stigmas.*—Color: Greenish-white.

Form: Bush.

Growth: Vigorous; dwarf; upright; branching; and compact.

Foliage: Number of leaflets on normal mid-stem leaves: 5.

*Size.*—Small (3½"×2¾").

*Quantity.*—Abundant.

*Color.*—New foliage: Light green. Old foliage: Upper surface: Green Group 138A; Lower surface: Green Group 138C.

Leaflets:

*Shape.*—Pointed oval.

*Texture.*—Upper side: Leathery.

*Edge.*—Serrated.

*Serration.*—Single and small.

*Petiole rachis.*—Color: Green.

*Petiole underside.*—Smooth, with 1 or 2 prickles.

*Stipules.*—Short (¼").

*Disease resistance.*—Resistant to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short (⅛") and straight.

*Color when young.*—Green.

Small prickles:

*Quantity.*—On main stalks: None. On laterals: None.

I claim:

1. A new and distinct variety of rose plant of the miniature class, substantially as herein shown and described, characterized particularly as to novelty by the unique combination of its long shelf life as a pot rose; its compact habit; its clustering ability; its ease of propagation by softwood cuttings; and its slightly larger flowers and leaves than POULvic.

* * * * *

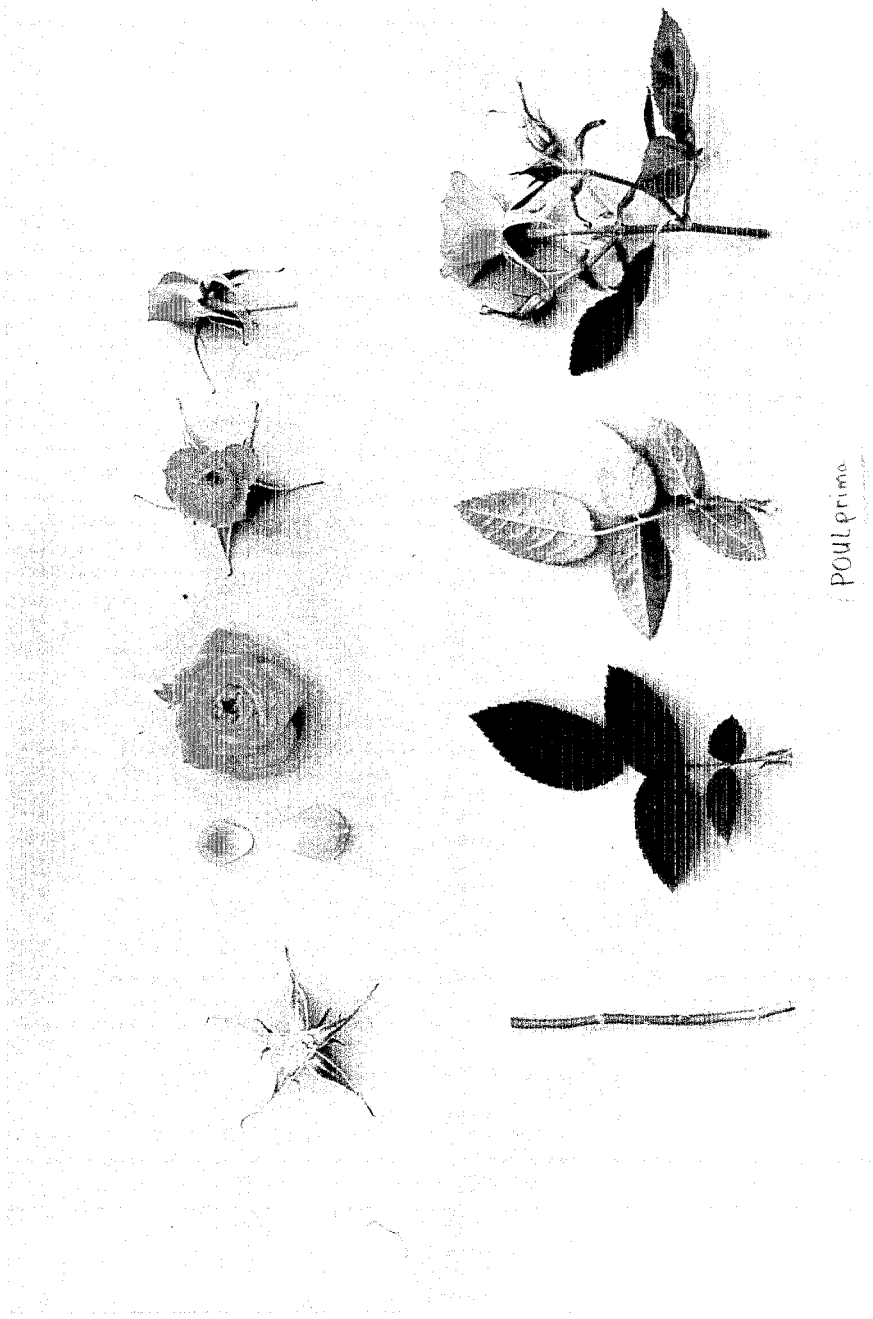
POULprima